United States Patent [19]
Witzel et al.

[11] Patent Number: 5,463,130
[45] Date of Patent: Oct. 31, 1995

[54] PREPARATION OF PERALKYLATED AMINES

[75] Inventors: Tom Witzel, Ludwigshafen; Eberhard Fuchs, Frankenthal; Horst Zimmermann, Mannheim, all of Germany

[73] Assignee: BASF Aktiengesellschaft, Ludwigshafen, Germany

[21] Appl. No.: 395,596

[22] Filed: Feb. 28, 1995

[30] Foreign Application Priority Data

Mar. 7, 1994 [DE] Germany .................. 44 07 466.2

[51] Int. Cl.$^6$ ................................. C07C 209/48
[52] U.S. Cl. .................. 564/490; 544/404; 564/415; 564/463; 564/503; 564/511
[58] Field of Search .................. 564/490, 415, 564/463, 503, 511; 544/404

[56] References Cited

U.S. PATENT DOCUMENTS

| | | | |
|---|---|---|---|
| 2,166,183 | 7/1939 | Signaigo | 260/583 |
| 5,101,075 | 3/1992 | Käsbauer et al. | 564/490 |
| 5,239,120 | 8/1993 | Merger et al. | 564/454 |
| 5,296,633 | 3/1994 | Fouquay | 564/490 X |

FOREIGN PATENT DOCUMENTS

| | | |
|---|---|---|
| 1157637 | 7/1969 | United Kingdom . |
| 1157638 | 7/1969 | United Kingdom . |
| 1157639 | 7/1969 | United Kingdom . |

OTHER PUBLICATIONS

Studies in Surface Science and Catalysis, vol. 27 (1986) 105–144.
Ind. Tech. Bull., vol. 11 (1970) 19–24.
Catalysis of Organic Reactions, Marcel Dekker, Inc. New York (1992) p. 103.

*Primary Examiner*—Richard L. Raymond
*Attorney, Agent, or Firm*—John H. Shurtleff

[57] ABSTRACT

A process for the preparation of peralkylated amines of the general formula I

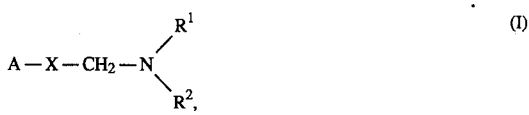

in which
$R^1$, $R^2$ denote $C_1$–$C_{200}$alkyl, $C_3$–$C_8$cycloalkyl, $C_4$–$C_{20}$alkylcycloalkyl, $C_4$–$C_{20}$ cycloalkylalkyl, $C_2$–$C_{20}$alkoxyalkyl, aryl, $C_7$–$C_{20}$alkylaryl, $C_7$–$C_{20}$aralkyl, $C_2$–$C_8$hydroxyalkyl, $C_2$–$C_8$mercaptoalkyl, $C_8$–$C_{20}$phenoxyalkyl, $C_2$–$C_8$ aminoalkyl, $C_2$–$C_8(NHR^4)$alkyl, $C_2$–$C_8(NR^4R^5)$alkyl or together form a saturated or unsaturated $C_2$–$C_6$alkylene chain optionally mono- to tri-substituted by $C_1$–$C_4$alkyl and optionally interrupted by oxygen or nitrogen
X denotes a $C_2$–$C_{20}$alkylene or $C_2$–$C_{20}$alkenylene or $C_4$–$C_8$cycloalkylene chain optionally mono- to pentasubstituted by $R^3$, $C_1$–$C_8$alkyl, $C_1$–$C_8$ alkoxy, $C_1$–$C_8$dialkylamino, phenoxy, diphenylamino and/or $C_2$–$C_8$ alkoxycarbonyl,
A denotes hydrogen, $C_1$–$C_{20}$alkyl, $C_3$–$C_8$cycloalkyl, $C_4$–$C_{20}$alkylcycloalkyl, $C_4$–$C_{20}$cycloalkylalkyl, $C_2$–$C_{20}$alkoxyalkyl, aryl, $C_7$–$C_{20}$alkylaryl, $C_7$–$C_{20}$ aralkyl, $C_1$–$C_{20}$alkoxy, hydroxy, $C_1$–$C_{20}$hydroxyalkyl, amino, $C_1$–$C_{20}$alkylamino, $C_2$–$C_{20}$dialkylamino, $C_3$–$C_{12}$alkenyleneamino, $C_3$–$C_8$cycloalkylamino, arylamino, aryl-$C_1$–$C_{12}$alkylamino, halogen, mercapto, $C_2$–$C_{20}$ alkenylenoxy, $C_3$–$C_8$cycloalkoxy and aryloxy
$R^3$ denotes $CH_2$—$NR^1R^2$,
$R^4$, $R^5$ denote $C_1$–$C_{20}$alkyl
by the reaction of a nitrile of the general formula II $$A\text{—}X\text{—}CN \qquad (II),$$

in which $R^1$, $R^2$, $R^4$, $R^5$, X and A have the aforementioned meanings and $R^3$ stands for —$CH_2$—$NR^1R^2$ or cyano, with a secondary amine of the general formula III

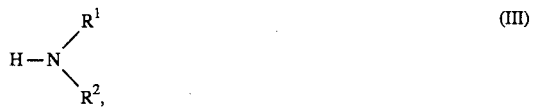

and hydrogen at temperatures ranging from 50° to 250° C. and pressures ranging from 5 to 350 bar in the presence of a catalyst, wherein the catalyst used is palladium on an oxidic support.

9 Claims, No Drawings

PREPARATION OF PERALKYLATED AMINES

The present invention relates to a process for the preparation of peralkylated amines from nitriles and secondary amines over a palladium catalyst at elevated temperatures and pressures.

Stud. Surf. Sci. Catal, 27 (1986) 105–144 describes, on page 123, the formation of tertiary amines from secondary amines and an aliphatic nitrile over a Pd/C catalyst. However the process is rejected with the argument that the reaction rate falls with increasing starting concentration of the secondary amine and only an unsatisfactory yield is achieved.

In addition, Ind. Tech. Bull, 11 (1970) 19–24 shows that there can be no expectation of a synthesis of tertiary amines from a secondary amine and a nitrile in a commercially useful yield. Although the tertiary amine tripentylamine is formed from valeronitrile at 84% selectivity when passed over Pd/C, the conversion amounts to only an unsatisfactory 28%. On the other hand, the secondary butylpentylamine is obtained over the same catalyst from valeronitrile and butylamine in 93% yield at 54% conversion. Despite the presence of secondary amine no tertiary amine is formed however.

Catalysis of Organic Reactions, Marcel Dekker, New York, Basel, 1992, p. 103, recommends the use of catalyst supports such as aluminum oxide for the preparation of primary amines, since the acid centers of the support adsorb amine already formed remote from the active centers and thus prevent linkage.

GB-A 1,157,637, GB-A 1,157,638 and GB-A 1,157,639 disclose the reaction of 2-methylglutarodinitrile with diethylamine in the presence of hydrogen and palladium on barium sulfate or preferably palladium on carbon to form 5-diethylamino-2-methylvaleronitrile. Despite the long reaction time and a diethylamine excess of 200 mol % no tetraethyl derivative was found, although the diethylamino group reacts not only with the nitrile groups in position 5 but also with that in position 1 (ratio 4 to 1). DE-A 3,935,641 describes the synthesis of a secondary amine over a palladium catalyst. The reaction of dimethylaminopropionitrile takes place in this case with itself under hydrogenating conditions to form bis(3-dimethylaminopropyl)amine. The formation of a tertiary amine is achieved only when a spinel is used as support material which is considerably expensive to produce, and the yield is not more than 58%.

U.S. Pat. No. 2,166,183 warns against the formation of cyclic secondary amines during the hydrogenation of dinitriles having 4, 5, or 6 carbon atoms: ie against the formation of hexamethyleneimine in the case of adipodinitrile.

It was thus the object of the present invention to overcome the aforementioned drawbacks.

Accordingly, we have found a novel and improved process for the preparation of a peralkylated amine of the general formula I

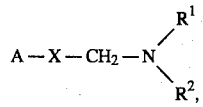

in which $R^1$, $R^2$ denote $C_1$–$C_{200}$alkyl, $C_3$–$C_8$cycloalkyl, $C_4$–$C_{20}$alkylcycloalkyl, $C_4$–$C_{20}$cycloalkylalkyl, $C_2$–$C_{20}$alkoxyalkyl, aryl, $C_7$–$C_{20}$alkylaryl, $C_7$–$C_{20}$aralkyl, $C_2$–$C_8$hydroxyalkyl, $C_2$–$C_8$ mercaptoalkyl, $C_8$–$C_{20}$phenoxyalkyl, $C_2$–$C_8$aminoalkyl, $C_2$–$C_8$ (NHR$^4$)alkyl, $C_2$–$C_8$ (NR$^4$R$^5$)alkyl or together form a saturated or unsaturated $C_2$–$C_6$alkylene chain optionally mono- to tri-substituted by $C_1$–$C_4$alkyl and optionally interrupted by oxygen or nitrogen X denotes a $C_2$–$C_{20}$alkylene or $C_2$–$C_{20}$alkenylene or $C_4$–$C_8$cycloalkylene chain optionally mono- to penta-substituted by $R^3$, $C_1$–$C_8$alkyl, $C_1$–$C_8$alkoxy, $C_1$–$C_8$dialkylamino, phenoxy, diphenylamino and/or $C_2$–$C_8$alkoxycarbonyl, A denotes hydrogen, $C_1$–$C_{20}$alkyl, $C_3$–$C_8$cycloalkyl, $C_4$–$C_{20}$alkylcycloalkyl, $C_4$–$C_{20}$cycloalkylalkyl, $C_2$–$C_{20}$alkoxyalkyl, aryl, $C_7$–$C_{20}$alkylaryl, $C_7$–$C_{20}$aralkyl, $C_1$–$C_{20}$alkoxy, hydroxy, $C_1$–$C_{20}$hydroxyalkyl, amino, $C_1$–$C_{20}$alkylamino, $C_2$–$C_{20}$dialkylamino, $C_3$–$C_{12}$alkenyleneamino, $C_3$–$C_8$cycloalkylamino, arylamino, aryl-$C_1$–$C_8$alkylamino, halogen, mercapto, $C_2$–$C_{20}$alkenylenoxy, $C_3$–$C_8$cycloalkoxy and aryloxy $R^3$ denotes $CH_2$—$NR^1R^2$, $R^4$, $R^5$ denote $C_1$–$C_{20}$alkyl by the reaction of a nitrile of the general formula II

in which $R^1$, $R^2$, $R^4$, $R^5$, X and A have the aforementioned meanings and $R^3$ stands for —$CH_2$—$NR^1R^2$ or cyano, with a secondary amine of the general formula III

and hydrogen at temperatures ranging from 50° to 250° C. and pressures ranging from 5 to 350 bar in the presence of a catalyst, wherein the catalyst used is palladium on an oxidic support.

The process of the invention can be carried out as follows:

The reaction of the nitriles [1 with the secondary amines III in the presence of hydrogen can be carried out at temperatures ranging from 50° to 250° C., preferably from 90° to 200° C. and more preferably from 120° to 160° C. and pressures of from 5 to 350 bar, preferably from 50 to 200 bar and more preferably from 70 to 150 bar batchwise or preferably continuously in pressure equipment such as autoclaves or tubular reactors or combinations thereof or preferably in a tubular reactor, over specific hydrogenation catalysts.

Suitable hydrogenation catalysts are palladium catalysts on oxidic supports. Suitable oxidic supports are, for example, γ-$Al_2O_3$, α-$Al_2O_3$, $SiO_2$, $TiO_2$, $ZrO_2$, α- or γ-$Al_2O_3$, $SiO_2$, $TiO_2$ or $ZrO_2$ doped with alkali metal oxides or alkaline earth metal oxides.

These palladium catalysts usually contain from 1 to 10 wt %, preferably from 3 to 5 wt % and more preferably from 5 to 1 wt % of palladium, based on the total weight of the catalyst.

The palladium catalysts are well known or can be prepared by generally known processes, for example, by impregnation of the support with palladium compounds such as $PdCl_2$ or $Pd(NO_3)_2$.

The molar ratio of secondary amine III to the nitrile II is usually from 1:1 to 30:1, preferably from 1:1 to 15:1 and more preferably from 11:1 to 5:1. However it is possible to use an even greater excess of amine or alternatively an excess of nitrile.

The process of the invention can be carried out without the use of a solvent or in a solvent such as water, methanol, ethanol, tetrahydrofuran, and methyl-tert-butyl ether. The solvents can also contain dissolved ammonia or the secondary amine II.

The peralkylated amines I obtained in the process of the invention can be purified in known manner, for example, by distillation.

The link X and the substituents A, $R^1$, $R^2$, $R^4$ and $R^5$ in the compounds I, II and III have independently the following meanings:

$R^1$, $R^2$ $C_1$–$C_{200}$alkyl, preferably $C_1$–$C_8$alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, n-decyl, 2-n-propyl-n-heptyl, n-tridecyl, 2-n-butyl-n-nonyl and 3-n-butyl-n-nonyl and more preferably isopropyl, 2-ethylhexyl, n-decyl, 2-n-propyl-n-heptyl, n-tridecyl, 2-n-butyl-n-nonyl and 3-n-butyl-n-nonyl, and preferably $C_{40}$–$C_{200}$alkyl such as polybutyl, polyIsobutyl, polypropyl, polyIsopropyl and polyethyl and more preferably polybutyl and polyIsobutyl,

A, $R^4$, $R^5$ $C_1$–$C_{20}$alkyl, preferably $C_1$–$C_{12}$alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl and more preferably $C_1$–$C_4$alkyl such as methyl, ethyl, n-propyl, isopropyl, n-butyl, isobutyl, sec-butyl and tert-butyl, $R^1$, $R^2$, A $C_3$–$C_8$cycloalkyl such as cyclopropyl, cyclobutyl, cyclopentyl, cyclohexyl, cycloheptyl and cyclooctyl preferred cyclopentyl, cyclohexyl and cyclooctyl and more preferably cyclopentyl and cyclohexyl, $C_4$–$C_{20}$alkylcycloalkyl, preferably $C_4$–$C_{12}$alkylcycloalkyl, $C_4$–$C_{20}$cycloalkylalkyl, preferably $C_4$–$C_{12}$cycloalkylalkyl, $C_2$–$C_{20}$alkoxyalkyl, preferably $C_2$–$C_8$alkoxyalkyl such as methoxymethyl, 2-methoxyethyl, 2-ethoxyethyl, 3-methoxypropyl and 3-ethoxypropyl, aryl such as phenyl, 1-naphthyl and 2-naphthyl, preferably phenyl, $C_7$–$C_{20}$alkylaryl such as $C_7$–$C_{20}$phenylalkyl, preferably $C_7$–$C_{12}$phenylalkyl such as benzyl, 1-phenethyl, 2-phenethyl, 1-phenylpropyl, 2-phenylpropyl, 3-phenyl-propyl, 1-phenylbutyl, 2-phenylbutyl, 3-phenylbutyl and 4-phenylbutyl and more preferably benzyl, 1-phenethyl and 2-phenethyl, $C_7$–$C_{20}$aralkyl, preferably $C_7$C_2$phenylalkyl such as benzyl, 1-phenethyl, 2-phenethyl, 1-phenylpropyl, 2-phenylpropyl, 3-phenyl-propyl, 1-phenylbutyl, 2-phenylbutyl, 3-phenylbutyl and 4-phenylbutyl and more preferably benzyl, 1-phenethyl and 2-phenethyl, $R^1$, $R^2$ $C_2$–$C_8$hydroxyalkyl, preferably $C_2$–$C_4$hydroxyalkyl such as 1-hydroyethyl, 2-hydroxyethyl, 2-hydroxy-n-propyl and 3-hydroxy-n-propyl, $C_2$–$C_8$mercaptoalkyl, preferably $C_2$–$C_4$mercaptoalkyl such as 1-mercaptoethyl, 2-mercaptoethyl, 2-mercapto-n-propyl and 3-mercapto-n-propyl, $C_8$–$C_{20}$phenoxyalkyl, preferably $C_8$–$C_{12}$phenoxyalkyl such as 2-phenoxyethyl, 2-phenoxypropyl, 3-phenoxypropyl, 2-phenoxybutyl, 3-phenoxybutyl and 4-phenoxy-butyl and more preferably 2-phenoxyethyl, $C_2$–$C_8$aminoalkyl, preferably $C_2$–$C_4$aminoalkyl such as 1-aminoethyl, 2-aminoethyl, 2-amino-n-propyl and 3-amino-n-propyl, $C_2$–$C_8$(NHR$^4$)alkyl, preferably $C_2$–$C_4$(NHR$^4$)alkyl such as (NHR$_4$)-methyl, (NHR4)-1-ethyl and (NHR$^4$)-2-ethyl, $C_2$–$C_8$(NR$^4$R$^5$)alkyl, preferably $C_2$–$C_4$(NR$^4$R$^5$)alkyl such as (NR$^4$R$^5$)-methel, (NR$^4$R$^5$)-1-ethyl and (NR$^4$R$^5$)-2-ethyl or they together form a saturated or unsaturated $C_2$–$C_6$alkylene chain optionally mono- to tri-substituted by $C_1$–$C_4$alkyl and optionally interrupted by oxygen or oxygen or nitrogen such as —$CH_2$—O—$CH_2$—$CH_2$—,
—$CH_2$—$CH_2$—O—$CH_2$—$CH_2$—,
—$CH_2$—$CH_2$—O—$CH_2$—$CH_2$—$CH_2$—,
—$CH_2$—$CH_2$—$CH_2$—O—$CH_2$—$CH_2$—$CH_2$—,
—$CH_2$—N—$CH_2$—$CH_2$—,
—$CH_2$—$CH_2$—N—$CH_2$—$CH_2$—,
—$CH_2$—$CH_2$—N—$CH_2$—$CH_2$—$CH_2$—,
—$CH_2$—$CH_2$—$CH_2$—N—$CH_2$—$CH_2$—$CH_2$—,
—$CH_2$—$CH_2$—NH—$CH_2$—$CH_2$—$CH_2$—$CH_2$—
N($CH_3$)— $CH_2$—$CH_2$—,
—$CH_2$—$CH_2$—N($CH_2CH_2$)—$CH_2$—$CH_2$— and
—$CH_2$—CH($CH_3$)—O—CH($CH_3$)—$CH_2$—,

X a $C_2$–$C_{20}$alkylene or $C_2$–$C_{20}$alkenylene or $C_4$–$C_8$cycloalkylene chain optionally mono- to penta-substituted by $R^3$, $C_1$–$C_8$alkyl, $C_1$–$C_8$alkoxy, $C_1$–$C_8$dialkylamino, phenoxy, diphenylamino and/or $C_2$–$C_8$alkoxycarbonyl, preferably a $C_2$–$C_8$alkylene chain optionally mono- to tri-substituted by $C_1$–$C_8$alkyl such as —($CH_2$)$_2$—, —($CH_2$)$_3$—, —($CH_2$)$_4$—, —($CH_2$)$_5$—, —($CH_2$)$_6$—, —($CH_2$)$_7$—, —($CH_2$)$_8$—, —CH($CH_3$)—$CH_2$—$CH_2$—, —$CH_2$—CH($CH_3$)—$CH_2$—, —$CH_2$—C($CH_3$)$_2$—$CH_2$—, preferably —($CH_2$)$_2$—, —($CH_2$)$_3$—, —($CH_2$)$_4$—, —($CH_2$)$_6$—, —$CH_2$—CH($CH_3$)—$CH_2$—$CH_2$—, —$CH_2$—C($CH_2$)—Ch$_2$—$CH_2$—, —$CH_2$—$CH_2$—CH(CN)—$CH_2$—$CH_2$—$CH_2$— and more preferably —($CH_2$)$_4$—,

A hydrogen, $C_1$–$C_{20}$alkoxy, preferably $C_1$–$C_8$alkoxy such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy, isooctoxy and more preferably $C_1$–$C_4$alkoxy such as methoxy, ethoxy, n-propoxy, isopropoxy, n-butoxy, isobutoxy, sec-butoxy and tert-butoxy, hydroxy, $C_1$–$C_{20}$hydroxyalkyl, preferably $C_1$–$C_8$hydroxyalkyl and more preferably $C_1$–$C_4$hydroxyalkyl such as hydroxymethyl, 1-hydroyethyl, 2-hydroxyethyl, 2-hydroxy-n-propyl and 3-hydroxy-n-propyl, amino, $C_1$–$C_{20}$alkylamino, preferably $C_1$–$C_8$aminoalkyl and more preferably $C_1$–$C_4$aminoalkyl such as methylamino, 1-aminoethyl, 2-aminoethyl, 2-amino-n-propyl and 3-amino-n-propyl,
$C_2$–$C_{20}$dialkylamino, preferably $C_2$–$C_{12}$alkylamino, particularly $C_2$–$C_8$dialkylamino such as
N,N-dimethylamino,
N,N-diethylamino,
N,N-dipropylamino,
N,N-di(1-methylethyl)amino,
N,N-dibutylamino,
N,N-di(1-methylpropyl)amino,
N,N-di(2-methylpropyl)amino,
N,N-di(1,1-dimethylethyl)amino,
N-ethyl-N-methylamino,
N-methyl-N-propylamino,
N-methyl-N-(1-methylethyl)amino,
N-butyl-N-methylamino,
N-methyl-N-(1-methyl-propyl)amino,
N-methyl-N-(2-methylpropyl)amino,
N-(1,1-dimethylethyl)-N-methylamino,
N-ethyl-N-propyl amino,
N-ethyl-N-(1-methyl-ethyl)-amino,
N-butyl-N-ethylamino,
N-ethyl-N-(1-methylpropyl)amino,
N-ethyl-N-(2-methylpropyl)amino,
N-ethyl-N-(1,1-dimethylethyl)-amino,
N-(1-methylethyl)-N-propylamino,
N-butyl-N-propylamino,
N-(1-methylpropyl)-N-propylamino,
N-(2-methylpropyl)-N-propylamino,
N-(1,1-dimethylethyl)-N-propylamino,
N-butyl-N-(1-methylethyl)amino,
N-(1-methylethyl)-N-(1-methylpropyl)amino,
N-(1-methylethyl)-N-(2-methylpropyl)amino,
N-(1,1-dimethylethyl)-N-(1-methylethyl)amino,
N-butyl-N-(1-methylpropyl)amino,
N-butyl-N-(2-methylpropyl)amino,
N-butyl-N-(1,1-dimethylethyl)amino,
N-(1-methylpropyl)-N-(2-methylpropyl)amino,
N-(1,1-dimethylethyl)-N-(1-methylpropyl)amino and
N-(1,1-dimethylethyl)-N-(2-methylpropyl)amino,
$C_3$–$C_{12}$azacycloalkyl, preferably $C_3$–$C_8$azacycloalkylamino and more preferably $C_5$–$C_8$azacycloalkyl such as pyrrolidine, piperidine, azepane, piperazine, N-alkylpiperazine and morpholine,
$C_3$–$C_8$cycloalkylamino such as cyclopropylamino, cyclobutylamino, cyclopentylamino, cyclohexylamino, cycloheptylamino and cyclooctylamino, preferably cyclopentylamino, cyclohexylamino and cyclooctylamino and more preferably cyclopentylamino and cyclohexylamino,
$C_3$–$C_8$dicycloalkylamino,
arylamino such as phenylamino, 1-naphthylamino and 2-naphthylamino, preferably phenylamino,
aryl-$C_1$–$C_8$alkylamino, preferably phenyl-$C_1$–$C_8$alkylamino and more preferably phenyl-$C_1$–$C_4$alkylamino such as phenyl/methylamino and phenyl/ethylamino,
halogen, preferably fluorine, chlorine and bromine and more preferably fluorine and chlorine,
mercapto, —SH,
$C_2$–$C_{20}$oxacycloalkyl, preferably $C_2$–$C_8$oxacycloalkyl and more preferably $C_2$–$C_8$oxacycloalkyl such as 2-tetrahydrofuranyl, 3-tetrahydrofuranyl, 2-furanyl and 3-furanyl
$C_3$–$C_8$cycloalkoxy such as cyclopropoxy, cyclobutoxy, cyclopentoxy, cyclohexoxy, cycloheptoxy and cyclooctoxy, preferably cyclopentoxy, cyclohexoxy and cyclooctoxy and more preferably cyclopentoxy and cyclohexoxy,
aryloxy such as phenoxy, 1-naphthoxy and 2-naphthoxy, preferably phenoxy.

The substituent $R^3$ in the compounds I denotes —$CH_2$—$NR^1R^2$, and in the compounds II the substituent $R^3$ stands for —$CH_2$—$NR^1R^2$ or cyano, preferably cyano. Such compounds I and II are preferred in which A is not hydrogen when X carries a —C(CN)— group in α-position to the substituent A.

Preferred nitrile compounds II are:
Acetonitrile, propionitrile, isopropionitrile, valeronitrile, pentenic acid nitrile, retenic acid nitrile, 3-hydroxypropionitrile, 3-methoxypropionitrile, 3-ethoxypropionitrile, 3-propoxypropionitrile, 3-isopropoxypropionitrile, 3-cyclohexoxypropionitrile, 2-methyl-3-hydroxypropionitrile, 3-methoxy-2-methylpropionitrile, 3-ethoxy-2-methylpropionitrile, 2-methyl-3-propoxypropionitrile, 3-isopropoxy-2-methylpropionitrile, 3-cyclohexoxy-2-methylpropionitrile, 3-methyl-3-hydroxypropionitrile, 3-methoxy-3-methylpropionitrile, 3-ethoxy-3-methylpropionitrile, 3-methyl-3-propoxypropionitrile, 3-isopropoxy-3-methylpropionitrile, 3-cyclohexoxy-3-methylpropionitrile, 3-aminopropionitrile, 3-methylaminopropionitrile, 3-dimethyl-aminopropionitrile, 3-ethylaminopropionitrile, 3-diethylaminopropionitrile, 3-propylaminopropionitrile, 3-dipropylaminopropionitrile, 3-isopropylaminopropionitrile, 3-diisopropylaminopropionitrile, 3-cyclohexylaminopropionitrile, 3-dicyclohexylaminopropionitrile, N-(cyanoethyl)-N-methylaniline. Snt particularly preferred compounds are 3-hydroxypropionitrile, 3-methoxypropionitrile, 3-dimethylaminopropionitrile, 3-diethylaminopropionitrile, 3-cyclohexylaminopropionitrile and 3-methylaminopropionitrile, preferably biscyanoethyl ether, biscyanoethylamine, N-methyl-bis-cyanoethylamine, n-ethylbiscyanoethylamine, n-N-propyl-biscyanoethylamine, n-N-propyl-biscyanoethylamine, polyIsobutylenenitrile, N-polyIsobutyleneaminopropionitrile, triscyanoethylamine, 5-aminovaleronitrile, 5-methylaminovaleronitrile, 5-dimethylaminovaleronitrile, 6-aminocapronitrile, 6-methylaminocapronitrile, 6-dimethylaminocapronitrile, 5-amino-4-methylvaleronitrile, 5-methylamino-4-methylvaleronitrile, 5-dimethylamino-4-methylvaleronitrile, 5-ethylamino-4-methylvaleronitrile, 5-diethylamino-4-methylvaleronitrile, 5-amino-2-methylvaleronitrile, 5-methylamino-2-methylvaleronitrile, 5-dimethylamino-2-valeronitrile, 5-ethylamino-2-methylvaleronitrile, 5-diethylamino-2-methylvaleronitrile, 4-cyanosuberoinitrile.

Preferred secondary amines III are:
Dimethylamine, diethylamine, dipropylamine, diisopropylamine, di-n-butylamine, diisobutylamine, di-sec-butylamine, di-2-ethylhexylamine, di-tridecylamine, dicyclohexylamine, ethylmethylamine, methylcyclohexylamine, ethylcyclohexylamine, piperazine, N-methylpiperizine, N-ethylpiperazine, diphenylamine, N-methylaniline, N-ethylaniline, diethanolamine, di-2-methoxyethylamine, di-2-ethoxyethylamin, methylethanolamine, ethylethanolamine, isopropylethanolamine, hydroxyethylaniline, particularly preferred compounds are dimethylamine, diethylamine and piperazine.

The tertiary amines I are curing agents for epoxy resins, catalysts for polyurethanes, intermediates for the preparation of quaternary ammonium compounds, plasticizers, corrosion inhibitors, textile auxiliaries, dyes and emulsifiers. Polyfunctionalized tertiary amines are also useful for the preparation of synthetic resins, ion exchangers, pharmaceuticals, plant protectants and pesticides.

EXAMPLES

Catalyst 1: 0.5 wt % of Pd on $Al_2O_3$ containing 20 wt % of CaO

Catalyst 2: 0.5 wt % of Pd: 5 wt % of Pr on $Al_2O_3$

Catalyst 3: 0.5 wt % of Pd on $Al_2O_3$

Example 1

Through a verticle hydrogenation reactor packed with 39 g of the catalyst 2 (diameter: 16 mm; packing to a height of 600 mm; oil-heated double-walled jacket), there was pumped upwardly from the bottom, under a pressure of 80 bar and at a temperature of 150° C., 101 mL/h of 3-dimethylaminopropionitrile and 10 mL/h of liquid dimethylamine (molar ratio 1:25). At the same time 10 L/h(STP) of hydrogen were passed upwardly through the reactor. Following depressurization to standard pressure and removal of the excess dimethylamine there were obtained after distillation 102 g/h (88%) of tetramethylpropylenediamine, bp: 144° to 148° C.,

Example 2

In the apparatus described in Example 1 there were obtained, over 47 g of catalyst 2 under a pressure of 80 bar and at a temperature of 150° C., from 184 mL/h of 3-hydroxypropionitrile and 23mL/h of dimethylamine (molar ratio 1:25) 22 g/h (83%) of 3-dimethylaminopropanol, bp: 82° to 84° C./5 mbar.

Example 3

In the apparatus described in Example 1 there were obtained, over 39 g of catalyst 1 under a pressure of 80 bar and at a temperature of 155° C., from 76 mL/h of 3-hydroxypropionitrile and 20mL/h of dimethylamine (molar ratio 1:25) 97 (89%) of 3-dimethylaminopropanol, bp: 82° to 84° C./5 mbar.

Example 4

In a pilot apparatus corresponding to the apparatus described in Example 1 (catalyst volume 800 mL) there were obtained, over 650 g of catalyst 3 under a pressure of 200 bar and at a temperature of 140° C., from 160mL/h of 3-hydroxypropionitrile and 193 mL/h of dimethylamine (molar ratio 1:12), 245 g/h (93%) of 3-dimethylaminopropanol, bp: 82° to 84° C./5 mbar.

Example 5

In an autoclave having a capacity of 300mL there were hydrogenated 43 g (0.5 mol) of piperazine and 14 g of 25% strength ammonium hydroxide solution and 31 g (0.75 mol) of acetonitrile over 10 g of catalyst 2 at 100° C. under 80 bar of hydrogen. The monoselectivity achieved a value of 96% at a piperazine conversion of 53%. If the reaction was allowed to go to a conversion of 100%, the selectivity was 65%. The catalyst could be used a number of times without loss of yield.

We claim:

1. A process for the preparation of a peralkylated amine of the general formula I

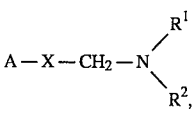

in which

R$^1$, R$^2$ denote $C_1-C_{200}$alkyl, $C_3-C_8$cycloalkyl, $C_4-C_{20}$alkylcycloalkyl, $C_4-C_{20}$ cycloalkylalkyl, $C_2-C_{20}$alkoxyalkyl, aryl, $C_7-C_{20}$alkylaryl, $C_7-C_{20}$aralkyl, $C_2-C_8$hydroxyalkyl, $C_2-C_8$mercaptoalkyl, $C_8-C_{20}$phenoxyalkyl, $C_2-C_8$ aminoalkyl, $C_2-C_8$(NHR$^4$)alkyl, $C_2-C_8$(NR$^4$R$^5$)alkyl or together form a saturated or unsaturated $C_2-C_6$alkylene chain optionally mono- to tri-substituted by $C_1-C_4$alkyl and optionally interrupted by oxygen or nitrogen X denotes a $C_2-C_{20}$alkylene or $C_2-C_{20}$alkenylene or $C_4-C_8$cycloalkylene chain optionally mono- to penta-substituted by R$^3$, $C_1-C_8$alkyl, $C_1-C_8$ alkoxy, $C_1-C_8$dialkylamino, phenoxy, diphenylamino and/or $C_2-C_8$ alkoxycarbonyl, A denotes hydrogen, $C_1-C_{20}$alkyl, $C_3-C_8$cycloalkyl, $C_4-C_{20}$alkylcycloalkyl, $C_4-C_{20}$cycloalkylalkyl, $C_2-C_{20}$alkoxyalkyl, aryl, $C_7-C_{20}$alkylaryl, $C_7-C_{20}$ aralkyl, $C_1-C_{20}$alkoxy, hydroxy, $C_1-C_{20}$hydroxyalkyl, amino, $C_1-C_{20}$alkylamino, $C_2-C_{20}$dialkylamino, $C_3-C_{12}$alkenyleneamino, $C_3-C_8$cycloalkylamino, arylamino, aryl-$C_1-C_8$alkylamino, halogen, mercapto, $C_2-C_{20}$ alkenylenoxy, $C_3-C_8$cycloalkoxy and aryloxy R$^3$ denotes $CH_2-NR^1R^2$, R$^4$, R$^5$ denote $C_1-C_{20}$alkyl by the reaction of a nitrile of the general formula II

in which R$^1$, R$^2$, R$^4$, R$^5$, X and A have the aforementioned meanings and R$^3$ stands for $-CH_2-NR^1R^2$ or cyano, with a secondary amine of the general formula III

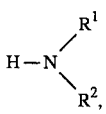

and hydrogen at temperatures ranging from 50° to 250° C. and pressures ranging from 5 to 350 bar in the presence of a catalyst, wherein the catalyst used is palladium on an oxidic support.

2. A process for the preparation of a peralkylated amine as defined in claim 1, wherein A does not denote hydrogen when X carries a $-C(CN)-$ group in α-position to the substituent A.

3. A process for the preparation of a peralkylated amine as defined in claim 1, wherein the oxidic support used is γ-$Al_2O_3$, α-$Al_2O_3$, $SiO_2$, $TiO_2$ or $ZrO_2$ or γ -$Al_2O_3$, α-$Al_2O_3$, $SiO_2$, $TiO_2$ or $ZrO_2$ doped with alkali or alkaline earth.

4. A process for the preparation of a peralkylated amine as defined in claim 1, wherein the catalyst contains from 1 to 10 wt % of palladium.

5. A process for the preparation of a peralkylated amine as defined in claim 1, wherein the catalyst contains from 3 to 5 wt % of palladium.

6. A process for the preparation of a peralkylated amine as defined in claim 1, wherein the secondary amine III is used in a molar ratio to the nitrile II of from 1:1 to 30:1.

7. A process for the preparation of a peralkylated amine as defined in claim 1, wherein the secondary amine III is used in a molar ratio to the nitrile II of from 1:1 to 15:1.

8. A process for the preparation of a peralkylated amine as defined in claim 1, wherein the secondary amine III is used in a molar ratio to the nitrile II of from 11:1 to 5:1.

9. A process for the preparation of a peralkylated amine as defined in claim 1, wherein the reaction is carried out at temperatures ranging from 90° to 200° C.

* * * * *